US00PP29774P3

(12) United States Plant Patent
Van Dijk

(10) Patent No.: US PP29,774 P3
(45) Date of Patent: Oct. 23, 2018

(54) ***ANTHURIUM* PLANT NAMED 'ANTHFYTWAL'**

(50) Latin Name: ***Anthurium andraeanum* L.**
Varietal Denomination: ANTHFYTWAL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 17 days.

(21) Appl. No.: 15/530,788

(22) Filed: Feb. 28, 2017

(65) Prior Publication Data

US 2018/0249614 P1 Aug. 30, 2018

(51) Int. Cl.
*A01H 6/00* (2018.01)
*A01H 5/02* (2018.01)

(52) U.S. Cl.
USPC ..... Plt./369
CPC ..... *A01H 6/00* (2018.05); *A01H 5/02* (2013.01)

(58) Field of Classification Search
USPC ..... Plt./369
See application file for complete search history.

*Primary Examiner* — Keith O. Robinson
(74) *Attorney, Agent, or Firm* — Jondle & Associates, P.C.

(57) ABSTRACT

A new *Anthurium* plant named 'ANTHFYTWAL' particularly distinguished by having unique red with white venation, ovate and durable spathes that retain the original color for a very long period of time, dark green and deltoid, durable leaves, purple-pink spadix with orange tip, early and rich flowering continuously throughout the year and a plant height of 32.0 cm to 35.0 cm, is disclosed.

3 Drawing Sheets

Genus and species: *Anthurium andraeanum* L.
Variety denomination: 'ANTHFYTWAL'.

BACKGROUND OF THE NEW PLANT

The present invention comprises a new and distinct variety of *Anthurium*, botanically known as *Anthurium andraeanum* L., and hereinafter referred to by the variety name 'ANTHFYTWAL'. The new *Anthurium* plant is a product of a planned breeding program conducted by the inventor in Bleiswijk, the Netherlands. The objective of this breeding program was to create a new plant with unique red and ovate spathes with white venation that flower continuously throughout the year.

The new variety originated from a cross-pollination made in March 2010 in Bleiswijk, The Netherlands. The female parent is a red with white venation *Anthurium* pot plant designated '18823-01' (unpatented), and the male parent was a cream with purple tip *Anthurium* pot plant designated '18376-03' (unpatented).

A single plant was selected from the progeny of the stated cross in June 2012 and has been asexually reproduced repeatedly by tissue culture in Bleiswijk, The Netherlands over a 3-year period. The present invention has been found to retain its distinctive characteristics through successive asexual propagations.

Plant Breeder's Rights for this variety have been applied for in the European Union on Nov. 24, 2015. 'ANTHFYTWAL' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Unique red spathe with white venation and green edge at the base;
2) Pink-purple spadix with orange tip; and
3) Green, deltoid leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 44-week old plant grown in a greenhouse in Bleiswijk, The Netherlands in January 2017. Colors in the photographs may differ from the color values cited in the detailed botanical description, which accurately describe the actual colors of the new variety.

DESCRIPTION OF THE NEW VARIETY

Figure 1:
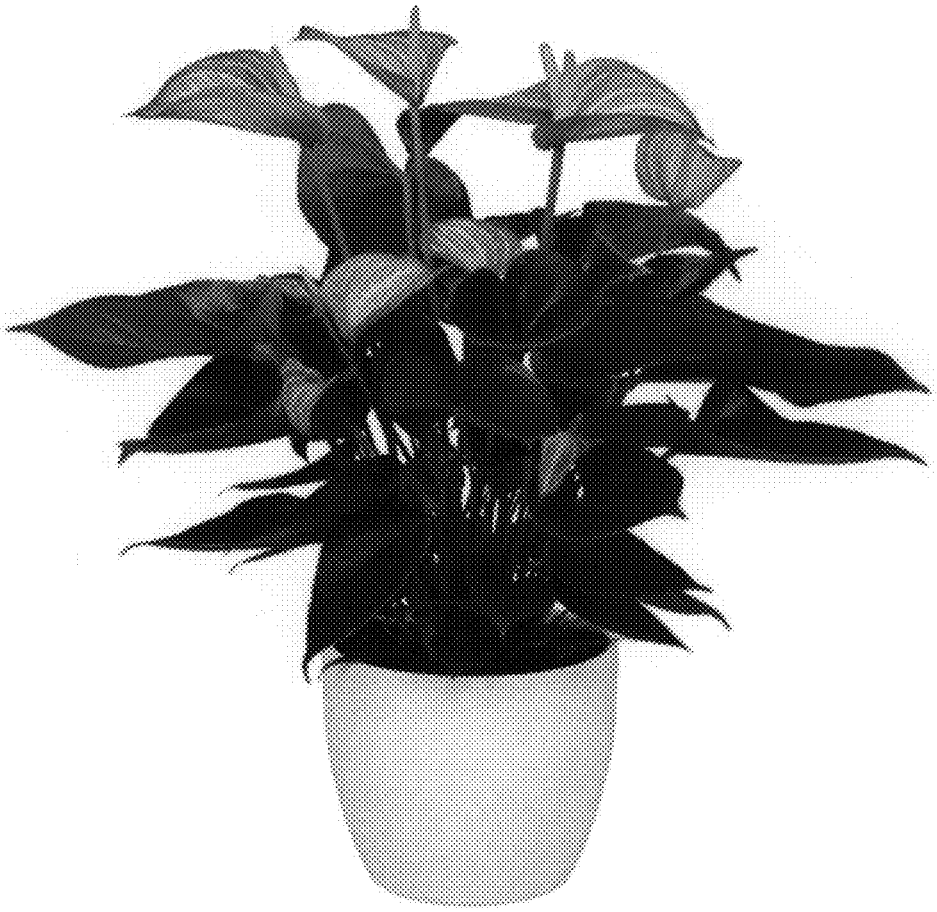
FIG. 1 shows the overall plant habit, including blooms and foliage.
Figure 2:
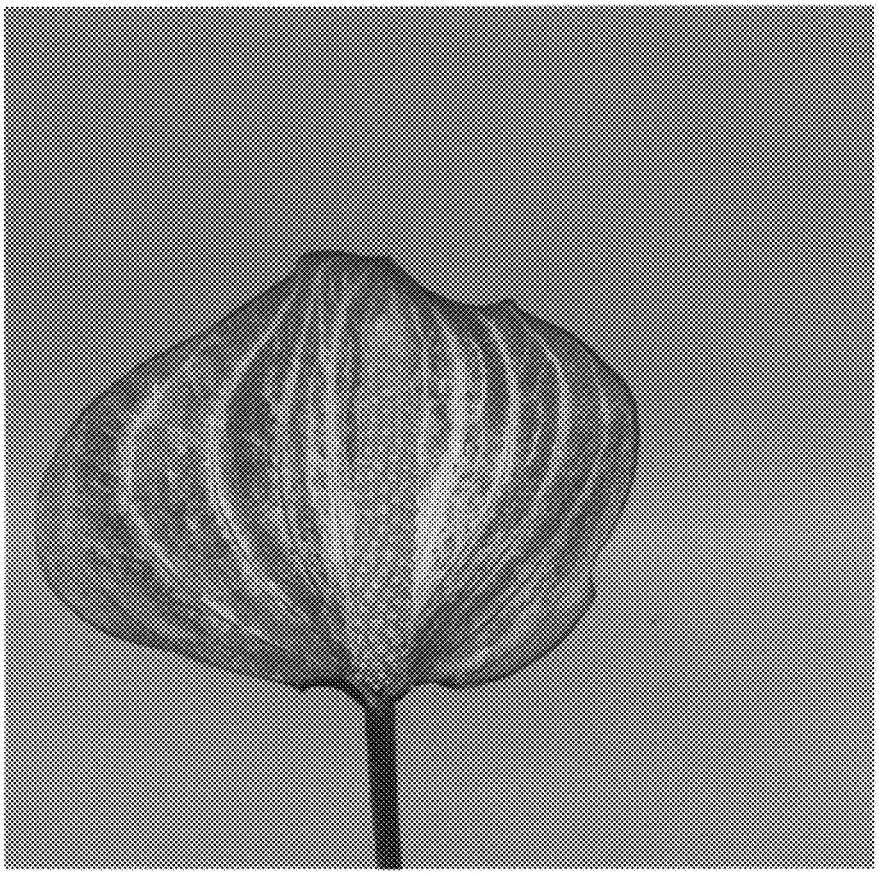
FIG. 2 shows a close-up of the mature spathe.
Figure 3:
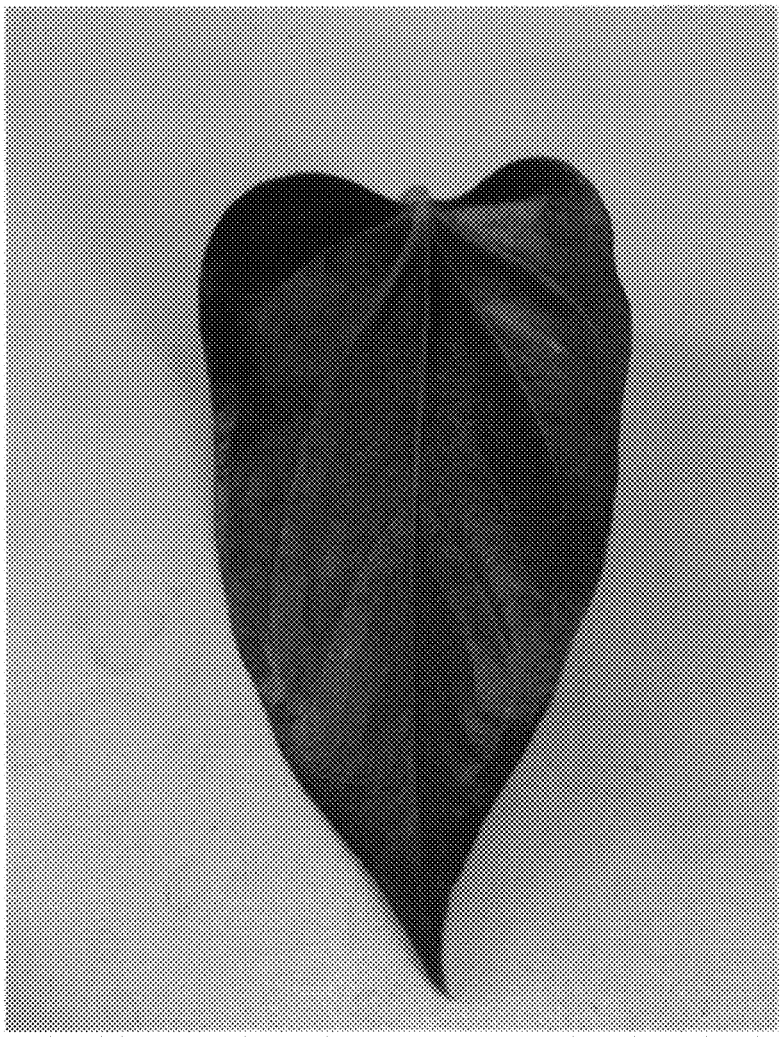
FIG. 3 shows a close-up of the upper leaf blade surface.

The following detailed description sets forth the distinctive characteristics of 'ANTHFYTWAL'. The data which define these characteristics were collected from asexual reproductions carried out in Bleiswijk, The Netherlands. The plant history was taken on 44-week old plants which were planted from tissue culture in 14-centimeter (diameter) pots and grown in a glass greenhouse between 19° C. and 24° C. Observations were made in January 2017. Color readings were taken under 5000 lux natural light in the greenhouse.

Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFYTWAL'.

Parentage:

*Female parent*.—*Anthurium* plant '18823-01' (unpatented).

*Male parent*.—*Anthurium* plant '18376-03' (unpatented).

Plant:

*Propagation*.—Tissue culture.

*Root description*.—Fleshy-creamy colored roots (RHS 158C) with small hairy lateral roots having yellow colored root tips (RHS 5B).

*Time to produce a finished flowering plant*.—42 to 46 weeks after planting in a 14 cm (diameter) pot.

*Growth habit*.—Herbaceous perennial.

*Height (measured from soil, including inflorescence)*.—32.0 cm to 35.0 cm.

*Width (measured from leaf tips)*.—40.0 cm to 44.0 cm.

Leaves:

*Immature leaves*.—Length: 10.0 cm to 14.0 cm. Width: 7.0 cm to 8.0 cm. Color: Upper surface: RHS 146A. Lower surface: RHS 146B. Texture (both upper and lower surfaces): Smooth and shiny.

*Mature leaves*.—Length (fully expanded): 14.0 cm to 17.0 cm. Width: 8.0 cm to 10.0 cm. Shape: Deltoid. Apex: Acuminate. Base: Cordate. Leaf blade angle with the petiole: Between 115 degrees and 130 degrees. Leaf margin: Entire. Color: Upper surface: RHS 147A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 147B. Lower surface: RHS 146C.

*Lobes*.—Present. Arrangement: Leaf blade has two lobes extending past the petiole. The lobes are non-touching. Length of lobes of mature leaf blades: 0.5 cm to 1.5 cm. Width of lobes of mature leaf blades: 2.5 cm to 3.5 cm. Distance for petiole/leaf junction to highest point on lobes of mature leaf blades: 2.5 cm to 3.5 cm.

*Petiole*.—Cross-section: Round. Diameter: 0.3 cm to 0.4 cm. Length: 12.0 cm to 15.0 cm for a mature leaf size. Color: Mature leaf: RHS 144A. Immature leaf: RHS 144B. Cataphyll color surrounding the petiole: Outside: RHS 144B. Inside: RHS 144C.

*Geniculum*.—Length: 1.7 cm to 2.2 cm. Width: 0.4 cm to 0.5 cm. Color: RHS 144B.

Inflorescence:

*Arrangement*.—Single.

*Flowering habit (length of flowering season)*.—Continuous.

*Number of inflorescences per plant*.—8 to 10.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 115 degrees and 125 degrees; the spathe stands on a wiry peduncle about 2.0 cm to 5.0 cm above the foliage.

*Shape*.—Ovate.

*Apex*.—Acuminate.

*Base*.—Ovate.

*Texture*.—Not blistered.

*Margin*.—Entire.

*Size*.—Length: 8.0 cm to 8.5 cm. Width: 8.0 cm to 9.0 cm.

*Lobes*.—Absent.

*Color*.—Just fully open: Upper surface: Red (RHS 53B) with white venation (RHS NN155B) and green edge (RHS 144A) toward the base. Lower surface: Pink (RHS 54C) with white venation (RHS NN155C) and green edge (RHS 144B) toward the base. This red color remains for a very long period, at least more than 30 weeks after opening.

Peduncle:

*Shape*.—Erect.

*Cross-section*.—Round.

*Length*.—22.0 cm to 26.0 cm.

*Diameter*.—0.35 cm to 0.4 cm.

*Color*.—RHS 144A.

Flowering time:

*General*.—One small rooted untreated tissue culture plant of 8.0 cm tall will flower, depending on season, after 42 to 44 weeks and 6 to 7 blossoms appear. More blossoms appear after some additional weeks so that a full flowering and commercial plant will have 7 to 8 red spathes. Smaller blossoms may occur on immature plants.

Spadix:

*Size*.—Length: 4.5 cm to 5.5 cm (depending on flower size). Width (at apex): 0.4 cm to 0.5 cm. Width (at base): 0.6 cm to 0.7 cm.

*Shape*.—Columnar.

*Curvature of longitudinal axis*.—Straight.

*Angle from spadix tip to peduncle*.—170 degrees to 180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 168B/C. Mature: RHS 186C. Ages to: RHS 181C/D.

Flowers:

*Quantity per spadix*.—150 to 200.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 54D.

Reproductive organs:

*Stamens*.—Not visible.

*Pollen amount*.—Absent.

*Pistil*.—Quantity: 150 to 200. Length: Less than 0.01 cm. Color: RHS 54D.

*Style*.—Not observed.

*Stigma*.—Shape: Ovoid. Diameter: Less than 0.01 cm. Color: RHS 54D.

*Ovary*.—Rarely visible.

*Ovary color*.—Not measured.

Fruit and seed set: None observed.

Disease and pest resistance: No specific resistance or susceptibility observed to pathogens and pests common to *Anthurium*.

COMPARISON WITH PARENTAL AND COMMERCIAL VARIETIES

'ANTHFYTWAL' differs from the female parent plant '18823-01' (unpatented) in that 'ANTHFYTWAL' has red spathes with white venation (RHS NN155B) and green toward the base, and purple-pink (RHS 186C) spadix with orange (RHS 168B/C) tips, whereas '18823-01' has red spathes with white venation (RHS NN155C), and light purple-pink (RHS 56B) spadix with orange (RHS 168D) tips. Additionally, 'ANTHFYTWAL' has shorter spadix than '18823-01'.

'ANTHFYTWAL' differs from the male parent plant '18376-03' (unpatented) in that 'ANTHFYTWAL' has red spathes with white venation and green toward the base, and purple-pink spadix with orange tips, whereas '18376-03' has white and purple spathes, and violet spadix with violet tips. Additionally, 'ANTHFYTWAL' has shorter spadix than '18376-03'.

'ANTHFYTWAL' differs from similar commercial variety 'ANTHDUXH' (U.S. Plant Pat. No. 27,731) in that 'ANTHFYTWAL' has red (RHS 53B), ovate spathes with white venation and green toward the base, and immature spadix with orange tips (RHS 168B/C), whereas 'ANTHDUXH' has red (RHS 45A), cordate spathes, and immature spadix with red tips (RHS 39A).

'ANTHFYTWAL' differs from similar commercial variety 'ANTHDUNDAL' (U.S. Plant Pat. No. 27,287) in that 'ANTHFYTWAL' has red (RHS 53B), ovate spathes with white venation and green toward the base, and immature spadix with orange tips, whereas 'ANTHDUNDAL' has red (RHS N45A), cordate spathes, and immature spadix with yellow tips. Additionally, 'ANTHFYTWAL' has deltoid shaped leaves, whereas 'ANTHDUNDAL' has elliptical cordate shaped leaves.

I claim:

1. A new and distinct variety of *Anthurium* plant named 'ANTHFYTWAL', substantially as illustrated and described herein.

* * * * *